United States Patent [19]

Cesarczyk

[11] Patent Number: 5,319,396
[45] Date of Patent: Jun. 7, 1994

[54] EYEGLASSES AND GOGGLES

[75] Inventor: Edward J. Cesarczyk, Boston, Mass.
[73] Assignee: Avitar, Inc., Canton, Mass.
[21] Appl. No.: 926,772
[22] Filed: Aug. 6, 1992
[51] Int. Cl.$^5$ ............................................. G02C 11/08
[52] U.S. Cl. ....................................... 351/62; 351/124
[58] Field of Search ................. 351/62, 124, 158, 133, 351/136

[56] References Cited

U.S. PATENT DOCUMENTS 3,133,982  5/1962  Janz ........................................ 351/62
4,934,807  6/1990  Bolléet al. ............................ 351/62

Primary Examiner—Richard A. Bertsch
Assistant Examiner—Alfred Basichas
Attorney, Agent, or Firm—Robert F. O'Connell

[57] ABSTRACT

An eye protective device having a frame member and a shield member attached to the frame member, the shield member having end portions which have tapered configurations. A pliant foam plastic member has a groove therein, the end portions of the groove having undercut tapered configurations which generally correspond to the tapered configurations of the end portions of the shield member. The tapered end portions of the groove engage the tapered end portions of the shield member so that the foam plastic member is held in place snugly against a wearer's face just above the eyes of the wearer during use so as to prevent perspiration or other debris from falling into the wearer's eyes.

8 Claims, 3 Drawing Sheets

EYEGLASSES AND GOGGLES

INTRODUCTION

This invention generally relates to eye protective devices, such as protective eyeglasses or goggles, and, more particularly, to eye protective devices having a pliable foam member for protecting the eyes from perspiration and/or other small debris, which member is readily attachable to and removable from the protective eye devices.

BACKGROUND OF THE INVENTION

Protective eyeglasses or goggles normally protect the eyes from matter which may directly strike the lenses and frames thereof, but often do not provide adequate protection from perspiration or other debris which may drip or fall into the eyes from a wearer's forehead, for example. Where such glasses may have some kind of protective element for that purpose, such element is usually permanently formed as a part of the overall frame structure or is affixed to the glass frames by an adhesive or other mechanical fastening device. When the protective element becomes worn or too soiled, it cannot be readily removed and often the glasses are simply discarded.

It is desirable to provide a pair of protective eyeglasses or goggles which can provide the latter protective function in a manner such that the protective mechanism therefor can be readily positioned on the glass frame structure and then readily removed when it becomes soiled or worn so that it can be easily and quickly replaced and the glasses themselves need not be discarded.

BRIEF SUMMARY OF THE INVENTION

In accordance with the invention, protective glasses or goggles comprise a frame having a protective shield member which, when worn, is positioned in front of the eyes of the wearer. Such shield member is preferably rotatably mounted on the frame and has a pair of appropriately disposed horizontal portions at either end thereof. A separate, molded, pliable foam plastic element is formed, as by using an injection molding technique. The pliable foam plastic element is configured so as to have an interior undercut region having dimensions which effectively correspond to the dimensions of the horizontal portions of the shield member. The plastic element can be readily affixed to the shield member so that the horizontal portions of the shield member easily fit into the undercut regions of the plastic element. The plastic element can just as readily be removed from the shield member by slipping it off from the horizontal portions of the shield member. The pliable member is preferably made of a hydrophilic polyurethane foam plastic material which readily absorbs moisture, such as perspiration from the wearer's forehead which may drip downwardly into contact therewith.

DESCRIPTION OF THE INVENTION

The invention can be described in more detail with the help of the accompanying drawings wherein.

Figure 1:
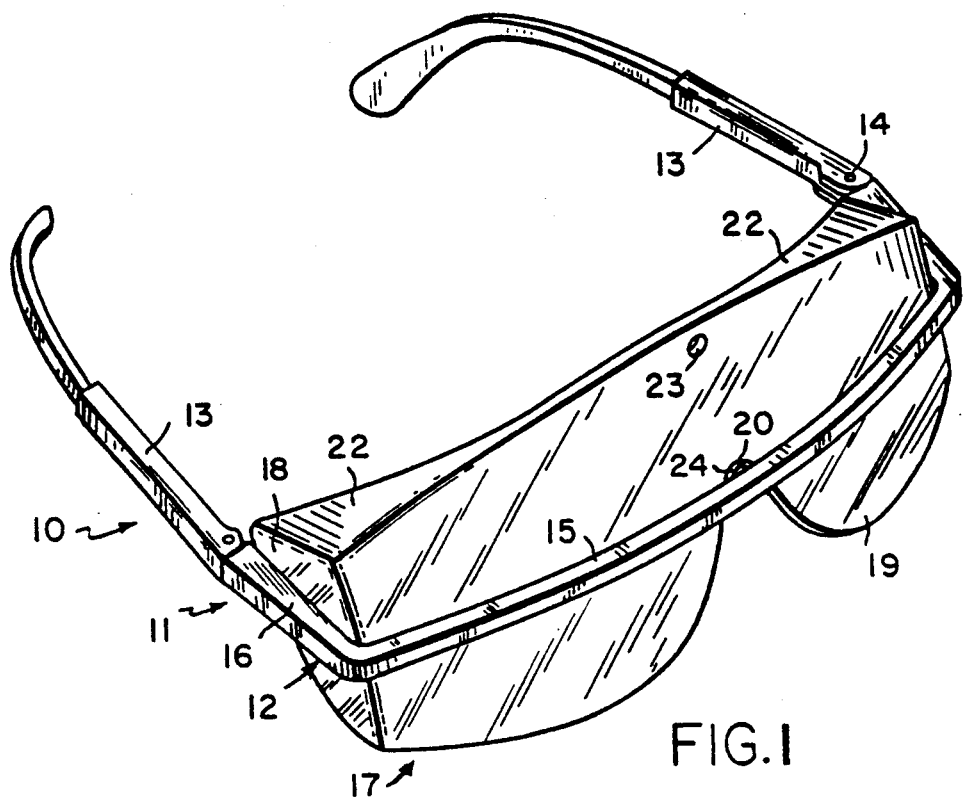
FIG. 1 shows a perspective view of a portion of the eye protection device of the invention.
Figure 2:
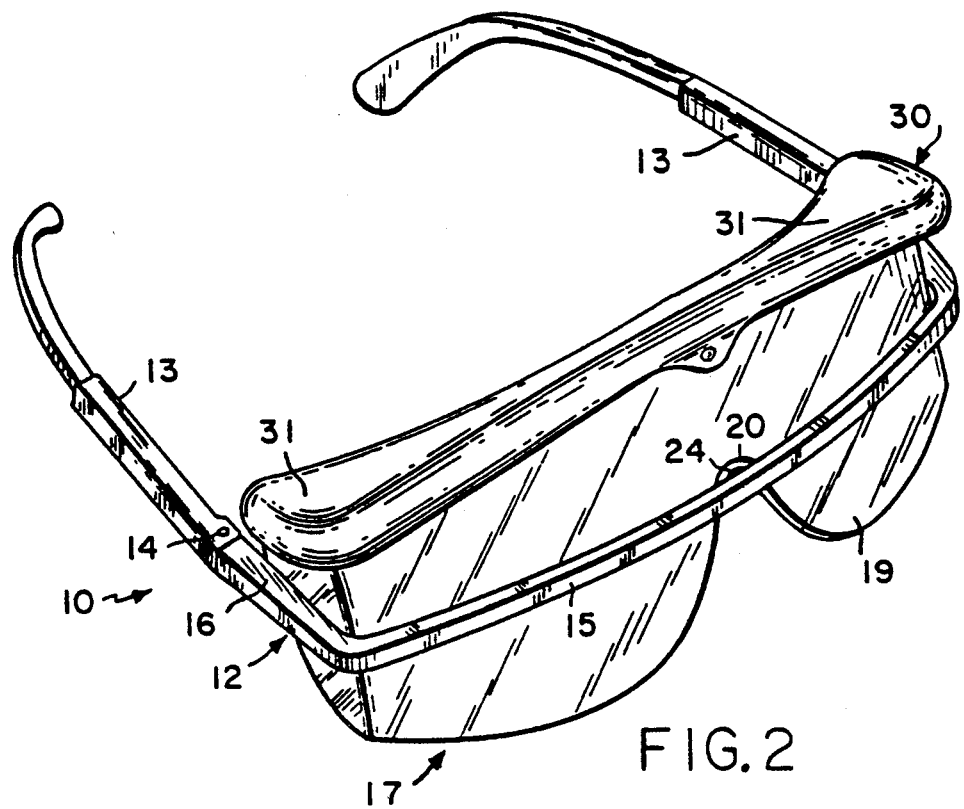
FIG. 2 shows a perspective view of the eye protective device of the invention with a foam plastic member engaged on to a shield member thereof.
Figure 3:
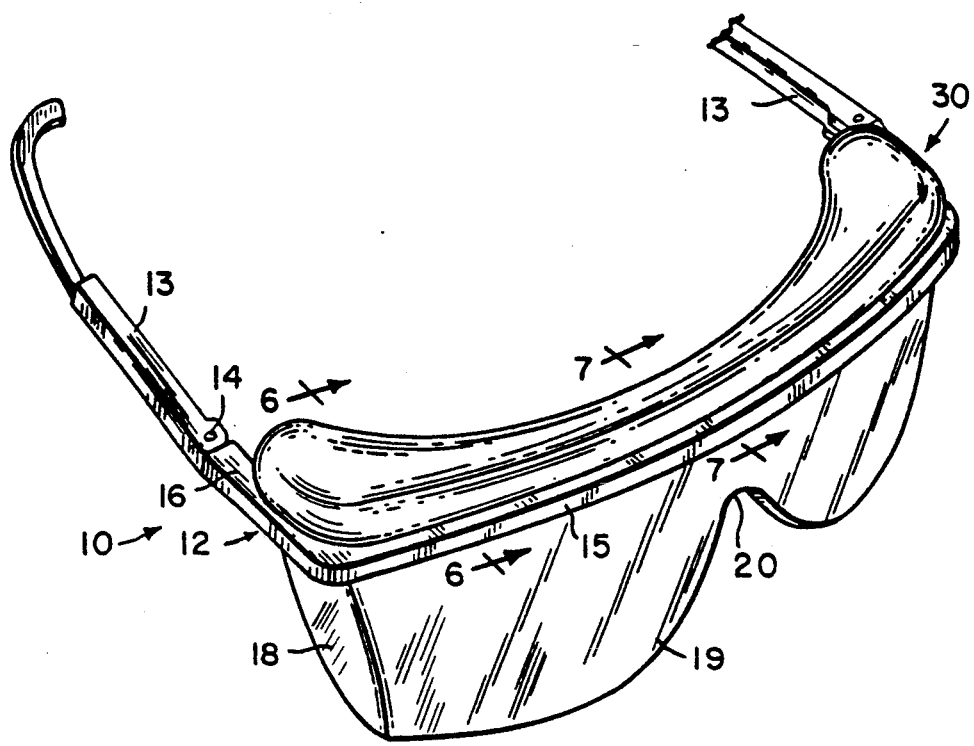
FIG. 3 shows a perspective view of the eye protective device of FIG. 2 with the frame member, foam plastic member, and shield member in place for use by a wearer.

As can be seen in FIGS. 1-3, a protective eyeglass structure 10, in accordance with a preferred embodiment of the invention, comprises a frame 11 having a front frame portion 12 and a pair of temple elements 13 rotatably attached thereto at rotation axes 14. The front frame portion includes an arcuate shaped element 15 extending across the wearer's face and integrally formed rearwardly projecting end portions 16 thereof at either side thereof. The oppositely disposed temple elements 13 are rotatably attached to the respective ends of projecting portions 16, as shown, at axes 14.

An arcuate-shaped, transparent shield member 17 is rotatably attached by vertical side tabs 18 to the inner surfaces of projecting end portions 16. Shield member 17 is configured so as to have a front portion 19 having a centrally located and suitably configured bridge 20 to fit over the nose of the wearer, the front portion 19 being disposed in front of the eyes of the wearer when worn. Shield member 17 further includes integrally formed, horizontal portions 22 along each side of the top thereof, such portions generally tapering outwardly from the central region of front portion 19 and extending at their widest points to a region at or near the inner ends of tabs 18. An aperture 23 at the top, center region of the front portion 19 of shield member 17 engages a small protuberance, or nib, 24 integrally formed at the top center of arcuate shaped element 15 above the bridge 20 (see FIG. 7), when the shield member is rotated to its operating position for wearing by a user.

Figure 4:
FIG. 4 shows a top plan view of the foam plastic member depicted in FIGS. 2 and 3.
Figure 5:
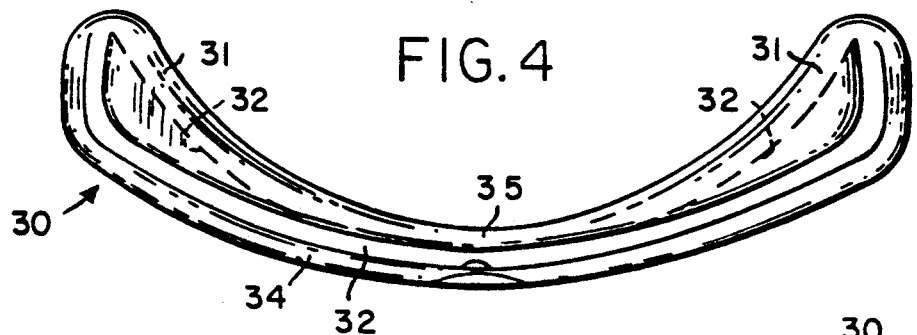
FIG. 5 shows a bottom plan view of the foam plastic member in FIG. 4.

FIGS. 4 and 5 show a top plan view and a bottom plan view, respectively, of a pliable foam plastic element 30 which has a generally arcuate shape substantially corresponding to that of the shield member 17. Plastic element 30 has widened end regions 31 having a shape generally corresponding to that of the tapered portions 22 of shield member 17. The pliable foam plastic element 30 is configured so as to have a groove 32 cut in the underside thereof extending from one end thereof to the other, the groove being undercut beneath the widened end regions 31, as shown by dashed line 32. Accordingly, at such end regions, the groove has a generally tapered configuration generally corresponding to the configuration of the tapered ends 22 of shield member 17.

Figure 6:
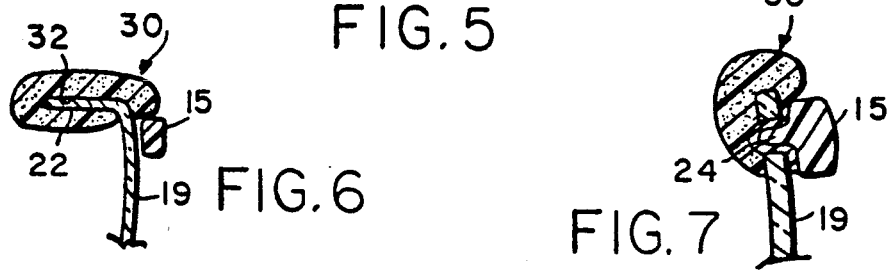
FIG. 6 shows a view in section along the line 6—6 of FIG. 3.
Figure 7:
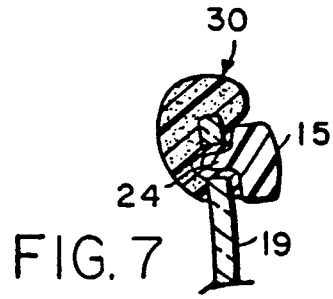
FIG. 7 shows a view in section along the line 7—7 of FIG. 3.

When the shield member 17 is rotated upwardly on frame 11, as shown in FIG. 1, the pliable foam plastic element 30 can be readily slipped on to the top of shield member 17 so that the tapered ends 22 engage the tapered undercut end regions 31 of the groove and the front and rear ridges 34 and 35 of the foam plastic element 30 engage the upper surface of shield member 17, as shown generally in FIG. 2 and more specifically in FIG. 6. The nib 24 at the top center of frame element 15 engages aperture 23 through the foam plastic material, as shown in FIG. 7, when the shield member is lowered into its operating position (FIG. 3). Accordingly, when the glasses are fully assembled with the foam plastic element 30 thereon, the latter is held firmly in place, without the need for adhesives or other mechanical fastening elements and snugly contacts the region of the wearer's face just above the eyes.

The foam plastic element is preferably made of a hydrophilic polyurethane foam plastic material, such as available from W. R. Grace & Co. of Lexington, Mass. under the designation HYPOL 2002. When it is in place on the wearer, the material readily absorbs moisture, such as perspiration, or other liquids which may be present, and prevents such moisture, as well as other particular debris that might be present on the forehead, from running down into the wearer's eyes. While such protective glasses are generally useful in many contexts, they can be particularly useful in specialized contexts, such as for sporting activities or in a medical environment, e.g., for use by surgeons or other hospital personnel in an operating room. In the latter case, the foam plastic element can be sterilized and used on a one-time, disposable basis and then discarded. The foam element can be made in a variety of colors and textures as suitable for the use being made of them, using injection molding and coloring techniques as would be well known to those in the art.

Figure 8:
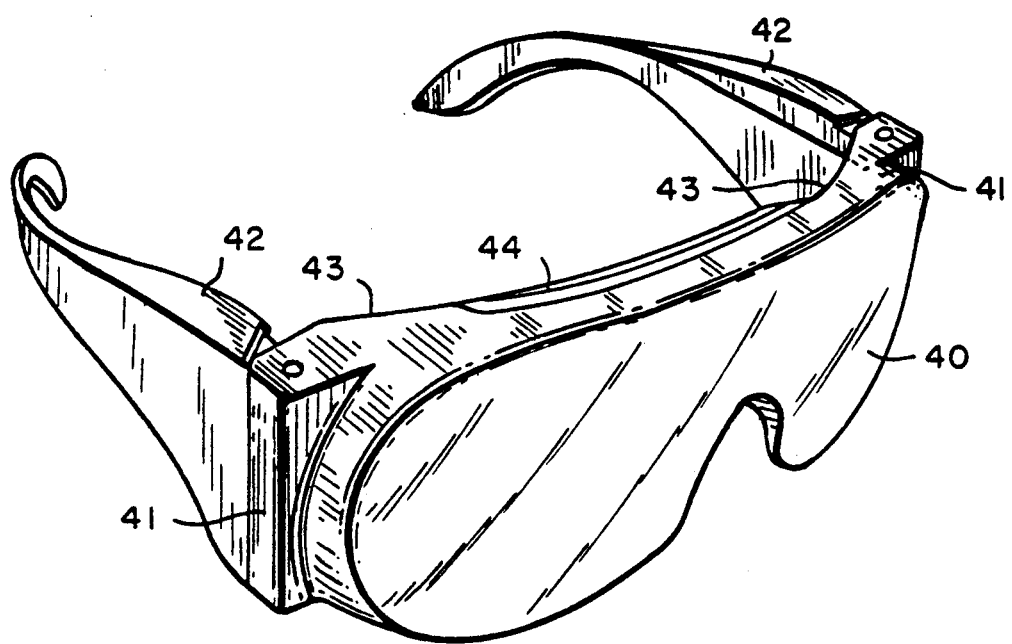
FIG. 8 shows a perspective view of another embodiment of an eye protection device for use in accordance with the invention.

In an alternative embodiment depicted in FIG. 8, a shield member 40 is integrally formed with frame member 41, the temples 42 being rotatably attached to frame member 41 as shown. The end portions 43 of the upper part of shield member 40 have generally tapered configurations which engage a pliant foam plastic member of the type shown in FIGS. 4 and 5 having a groove with similarly tapered undercuts at the ends thereof. A raised rib element 44 can optionally be formed at the central region of the upper part of shield member 40 to assist in engaging the central portion of the groove in the foam plastic member.

While the invention has preferred embodiments as disclosed above, modifications thereof may occur to those in the art within the spirit and scope of the invention and, hence, the invention is not to be construed as limited to such preferred embodiments, except as defined by the appended claims.

What is claimed is:

1. An eye protective device comprising
   a frame member;
   a shield member on said frame member, said shield member having end portions which have selected configurations;
   a pliant foam plastic member having a groove positioned therein, the end portions of said groove being undercut therein to form groove configurations which generally correspond to the selected configurations of the end portions of said shield member,
   whereby, during use, the end portions of said groove in said foam plastic member engage the end portions of said shield member, said foam plastic member being held in place and positioned snugly against a portion of a wearer's face above the wearer's eyes.

2. An eye protective device in accordance with claim 1 wherein the end portions of said shield member and of said groove have tapered configurations.

3. An eye protective device in accordance with claims 1 or 2 and further wherein the groove portion in said foam plastic member between the tapered end portions thereof engages a portion of said frame member.

4. An eye protective device in accordance with claim 1 wherein said shield member is rotatably attached to said frame member for rotation from a first position to a second position.

5. An eye protective device in accordance with claim 4 wherein, when said shield member is in said first position, said foam plastic member is engaged with the end portions thereof, and when said shield is in said second position, said foam plastic member is held in place and positioned snugly against said portion of a wearer's face.

6. An eye protective device in accordance with claim 5 wherein
   said shield member has an aperture positioned therein;
   said frame member has a corresponding nib fixedly positioned thereon whereby, during use, when said shield member is moved into its second position, the nib engages said aperture to hold said foam plastic member and said shield member firmly in said frame member.

7. An eye protective device in accordance with claim 1 wherein said shield member is integrally formed with said frame member.

8. An eye protective device in accordance with claim 1 wherein said foam plastic member is made of a hydrophilic polyurethane foam.

* * * * *